United States Patent [19]

Orlianges et al.

[11] Patent Number: 5,138,719
[45] Date of Patent: Aug. 18, 1992

[54] GLOVES, FINGER STALLS AND SIMILAR PROTECTIVE AND OPERATIONAL ARTICLES, AND PROCESSES FOR THEIR MANUFACTURE

[75] Inventors: Léo Orlianges, Boulogne; Gilles Argy, La Queue Les Yvelines; André Cheymol, Dangé-St. Romain, all of France

[73] Assignee: Hutchinson, S.A., Paris, France

[21] Appl. No.: 734,510

[22] Filed: Jul. 23, 1991

Related U.S. Application Data

[63] Continuation of Ser. No. 442,592, Nov. 28, 1989, abandoned.

[30] Foreign Application Priority Data

Dec. 1, 1988 [FR] France ................... 88 15748

[51] Int. Cl.$^5$ ............................. A41D 19/00
[52] U.S. Cl. ........................... 2/168; 2/169; 264/131; 264/305
[58] Field of Search ........... 2/2.5, 159, 161 R, 163, 2/164, 167, 168, 169, DIG. 7; 264/112, 131, 305, 309, DIG. 37

[56] References Cited

U.S. PATENT DOCUMENTS

| | | |
|---|---|---|
| 3,411,982 | 11/1968 | Kauglir et al. |
| 3,813,695 | 6/1974 | Podell, Jr. et al. |
| 3,911,501 | 10/1975 | Seltzer |
| 3,975,775 | 8/1976 | Alsop |
| 4,027,060 | 5/1977 | Esemplare et al. |
| 4,070,713 | 1/1978 | Stockum |
| 4,143,109 | 3/1979 | Stockum |
| 4,310,928 | 1/1982 | Joung |
| 4,329,312 | 5/1982 | Ganz |
| 4,519,098 | 5/1985 | Dunmire et al. |
| 4,575,476 | 3/1986 | Podell et al. |
| 4,742,578 | 5/1988 | Seid |
| 4,771,482 | 9/1988 | Shlenker |
| 4,779,290 | 10/1988 | Welch et al. |
| 4,853,978 | 8/1989 | Stockum |
| 4,864,661 | 9/1989 | Gimbel |
| 4,881,277 | 11/1989 | Hogle |
| 4,901,372 | 2/1990 | Pierce |
| 4,902,453 | 2/1990 | Okura et al. |
| 4,919,966 | 4/1990 | Shlenker |
| 4,930,522 | 1/1990 | Busnel et al. |
| 4,935,260 | 1/1990 | Shlenker |

FOREIGN PATENT DOCUMENTS

| | | |
|---|---|---|
| 232239 | 8/1987 | European Pat. Off. |
| 3135504 | 1/1988 | Japan |

*Primary Examiner*—William A. Cuchlinski, Jr.
*Assistant Examiner*—Scott W. Cummings
*Attorney, Agent, or Firm*—Bell, Seltzer, Park & Gibson

[57] ABSTRACT

The present invention relates to a glove, finger stall or the like comprised of a latex or other elastomeric material containing microcapsules. The glove or finger stall is characterized in that the concentration of microcapsules increases progressively from the outer surface, where the concentration equals 0, towards the inner surface of the glove contacting the skin of the user, where the concentration equals 90 to 95% of the microcapsules present.

15 Claims, 1 Drawing Sheet

GLOVES, FINGER STALLS AND SIMILAR PROTECTIVE AND OPERATIONAL ARTICLES, AND PROCESSES FOR THEIR MANUFACTURE

CROSS REFERENCE TO RELATED APPLICATIONS

This is a continuation application of Ser. No. 07/442,592, filed Nov. 28, 1989, now abandoned.

BACKGROUND OF THE INVENTION

The present invention relates to improvements in protective gloves or finger stalls used primarily by doctors, surgeons, hospital staff, researchers, technicians, etc.

At present, the type of glove most widely used is a latex glove which is easily sterilizable, completely aseptic, flexible, strong, adaptable to the shape of the hand, and possesses great tactile sensitivity. However, such gloves have two considerable drawbacks: difficulties with intromission and removal of the glove, and the risk of tearing by a or perforating by the needle of a syringe.

To counter the difficulty of intromission and to facilitate "slipping on" of the glove, various additives (e.g. particulate materials or powders such as talc or cornstarch) have been applied to the glove surface for lubrication, either by dusting the surface with such particulate materials or by adhering a layer of the particles to the surface as disclosed for example in U.S. Pat. No. 4,070,713. In addition, halogens have been used to chemically transform the surface of the glove that contacts the hand (so called "chlorination" treatments). Although providing a better slipping effect and easier fitting on, the use of particulate materials and halogen treatment often cause allergic reactions, which in certain cases may be serious.

While linings or textile supports have also been proposed, these solutions are expensive and the gloves obtained are difficult to handle.

At the present time, there is practically nothing on the market to protect against the risk of contamination from cutting or tearing of the glove.

In U.S. Pat. No. 4,930,522, there is disclosed a glove or finger stall which incorporates microcapsules containing pharmacological agents for protecting the user from contamination. The microcapsules are located between two layers of elastomer, and not along the inner, skin-contacting layer of the glove. Accordingly, the pharmacological agents are released only when both a layer of elastomer and the microcapsules are ruptured. In addition, the microcapsules of these gloves are not positioned to reduce the friction between the skin and glove by reducing the points of contact with the user's skin.

Consequently, it is an object of the present invention to provide a protective glove, finger stall or the like, which better responds to the necessities of practice than the gloves or finger stalls previously proposed according to the prior art.

It is a further object of the invention to provide a glove or finger stall of the type described which has substantially improved slipping properties without resorting to various additives or techniques which may cause allergic reactions.

It is still another object of the invention to provide a glove or finger stall of the type described which ensures for the user thereof an increased protection against microbes or other pathogens or against, for example, pricks due to the needle of a syringe.

SUMMARY OF THE INVENTION

According to the present invention, there is provided a protective glove, finger stall or the like characterized in that the latex or other elastomer from which it is formed contains microcapsules which are so disposed and arranged as to form a concentration gradient, with the concentration of such microcapsules increasing progressively from the outer surface to the inner surface thereof. Thus at the outer surface of the glove, finger stall or the like, the concentration equals zero, while at the inner surface, in contact with the skin of the user, the concentrations equals 90 to 95 percent of the microcapsules contained in the glove.

The relief surface formed by the high concentration of these microcapsules at the inner surface of the glove which contacts the skin ensures good sliding properties and thereby facilitates putting on the glove without the necessity of any additives, such as powders or chemical treatments as conventionally used in the prior art as noted above.

According to a particularly advantageous embodiment of the invention, the microcapsules, whose diameters vary between 10 and 100 microns, contain a suitable pharmacological agent. When the envelope of the microcapsule is punctured or ruptured, such as penetration of the glove by the needle of a syringe or tearing of the glove by a scalpel, the pharmacological protective agent is spread on both the needle or scalpel blade and on the area of skin affected. If desired, the size, thickness and fragility of the envelope of the microcapsules can be regulated so that simple friction releases the prophylactic pharmacological agent more or less easily. The microcapsules may contain different pharmacological agents having different but complementary properties.

The presence of the microcapsules gives an undulated contact surface which diminishes the points of contact with the user's skin and reduces the frictional or adherent forces between the skin and the glove. Accordingly, the glove can be more easily positioned on the hand.

According to another advantageous embodiment of the invention, the layer of latex or the like contains a dehydrating substance, such as an acrylic resin. The advantage of this embodiment is readily apparent, since wearing a medical glove often causes sweating. When the dehydrating substance is present, the microcapsules in the layer of latex or the like preferably contain a moisture-free pharmacological agent.

According to another particularly advantageous embodiment of the present invention, the layer of latex or the like contains, in areas devoid of microcapsules (i.e., the area where the concentration of microcapsules is nil) mechanical barriers protecting against needle pricks or scalpel cuts. Such mechanical barriers may comprise, for example, glass microdiscs, bamboo fibers, or carbon fibers.

Another object of the present invention is to provide a process for manufacturing the protective glove or finger stall as defined above and comprises the following steps:

immersing a mold in the desired shape of the glove or finger stall in a first bath of latex or similar elastomeric material devoid of microcapsules and forming on the mold a first layer of latex or similar elastomeric material devoid of microcapsules, immersing the thus formed layer in a second bath of elastomer containing the desired amount of microcapsules or dehydrating substance, the thickness of this part being a function of the duration of immersion, vulcanizing or hardening the thus formed layers, and then after vulcanization, stripping the glove, finger stall or the like from the mold and turning it inside out.

If desired, the first bath may be preceded by a coagulation bath. Also, the second bath may be preceded by vulcanization.

According to one mode of the invention, the microcapsules may be deposited on the latex by flocking or spraying before the latex is dried.

BRIEF DESCRIPTION OF THE DRAWINGS

In addition to the foregoing features, the invention comprises other features which will become evident from the following description, given by way of a non-limiting example referring to the accompanying drawings in which.

It must be well understood, however, that these drawings and the corresponding descriptive portions are given purely for illustration of the invention and do not in any way constitute a limitation.

DESCRIPTION OF PREFERRED EMBODIMENTS

Figure 1:
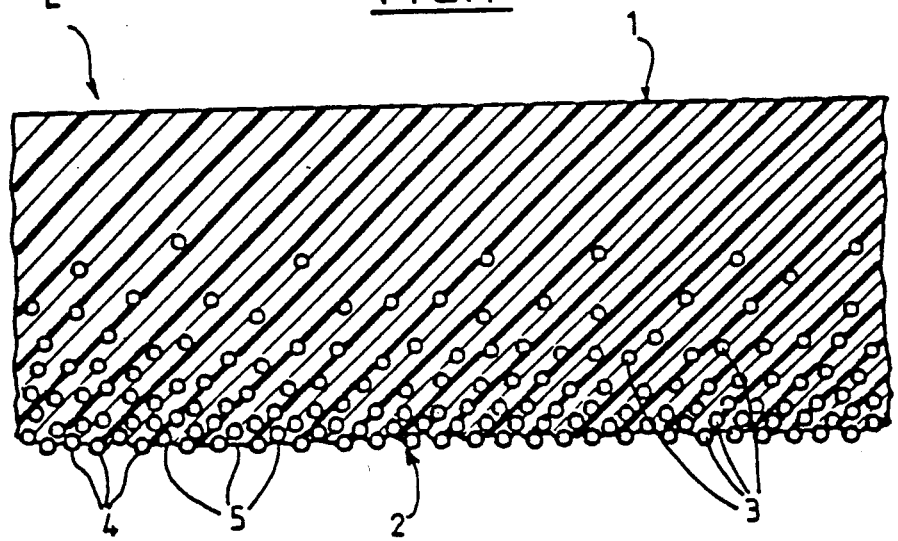
FIG. 1 shows, on a large scale, a section of one embodiment of the layer of latex according to the present invention.
Figure 2:
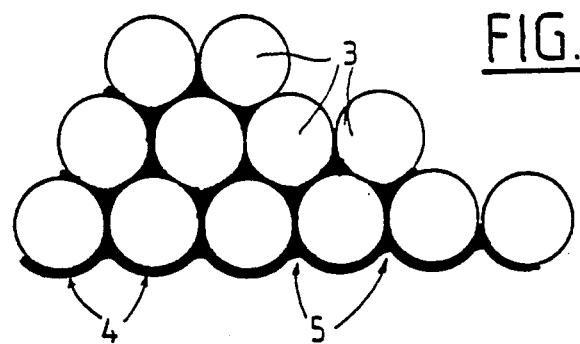
FIG. 2 shows a very enlarged portion of the inner surface of the glove.

As illustrated in FIG. 1, a latex layer L has an outer surface 1 which forms the external surface of the glove, finger stall or the like and an inner surface 2 which is applied against the skin of the user. Such inner surface 2 is made up of humps 5 and hollows 4, which are formed by the presence of microcapsules, microspheres, or microbeads 3 (which are better distinguished in FIG. 2).

Latex layer L was prepared in the following manner: A ceramic shape or mold is immersed in a latex bath and a layer of the latex is deposited on the mold. Then, after light drying, it is dipped in a bath formed of prevulcanized latex (for example, "Resultex" prevulcanized with sulphur) diluted to have a 35% solution of dry extract and into which the microcapsules 3 are introduced. The microcapsules are previously filled with the desired pharmacological agent. The immersion lasts 15 seconds to obtain a film of 180 microns thickness. After rinsing for 10 minutes in water at 40 degrees C., it is dried at room temperature for 2 hours.

Figure 3:
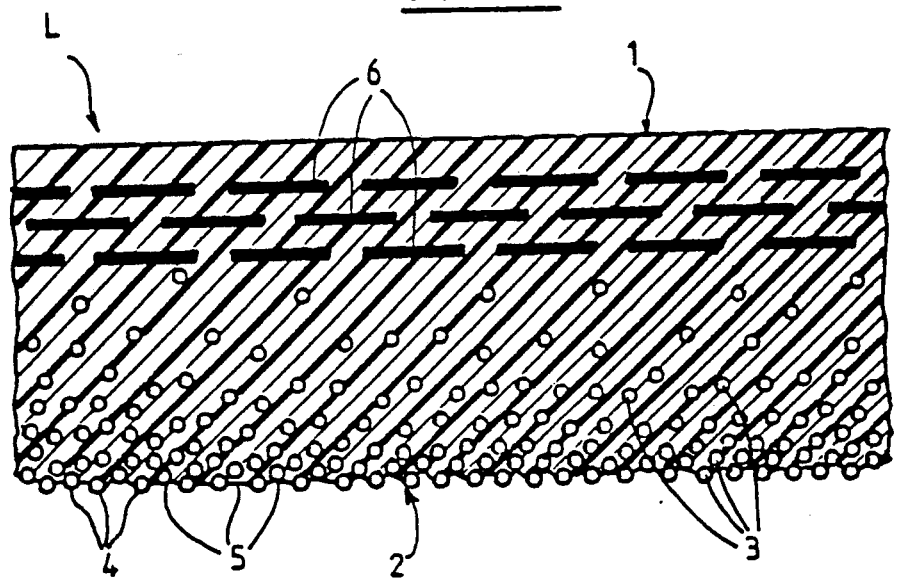
FIG. 3 shows another embodiment of a latex layer according to the present invention.

Another very interesting modification of this process consists of introducing microdiscs 6 of glass (or bamboo fibers or carbon fibers) as shown in FIG. 3.

From the preceding description, it is evident that, whatever the methods of practice, embodiments and uses adopted, protective gloves are obtained which slip on perfectly. This is due, in particular, to the presence of the humps 4 and the hollows 5. Such humps 4 also contain a pharmacological agent within the microcapsule 3. With respect to previously known protective gloves directed to the same purpose, these protective gloves have considerable advantages, certain of which have been mentioned earlier, and others of which that emerge from the use of said gloves, finger stalls or the like.

What is claimed is:

1. A protective glove or finger stall for use by medical and research persons which is constructed to have improved slipping properties to facilitate positioning on the hand and to also provide protection to the wearer against microbes or other pathogens, said glove or finger stall comprising a shaped elastomeric material having an inner surface and an outer surface; rupturable and puncturable microcapsules containing at least one pharmacological agent provided in said elastomeric material and being arranged therein so that the concentration thereof increases progressively from the outer surface to the inner surface, with the concentration at said inner surface being 90 to 95% of the total number of microcapsules present in the elastomeric material; and wherein said 90 to 95% concentration at said inner surface presents an undulated inner contact surface to reduce the points of contact with the user's skin so as to diminish the frictional or adherent forces between the skin and the glove thus making the placing and fitting of the glove or finger stall on the hand easy, the outer surface of said elastomeric material being free of the presence of said microcapsules.

2. A protective glove or finger stall according to claim 1, wherein said microcapsules have a diameter between 10 and 100 microns.

3. A protective glove or finger stall according to claim 1, wherein said pharmacological agent is moisture-free.

4. A protective glove or finger stall according to claim 1, wherein said elastomeric material contains a dehydrating substance.

5. A protective glove or finger stall according to claim 4, wherein said dehydrating substance comprises an acrylic resin.

6. A protective glove or finger stall according to claim 1, wherein said elastomeric material contains mechanical barriers.

7. A protective glove or finger stall according to claim 6, wherein said mechanical barriers comprise glass micro-discs, bamboo fibers or carbon fibers.

8. A protective glove or finger stall of claim 1, wherein said elastomeric material comprises an elastomeric latex.

9. A method of preparing a protective glove or finger stall, comprising:

immersing a mold in the desired shape of the glove or finger stall in a first bath of elastomeric material devoid of microcapsules and forming on the mold a first layer of elastomeric material devoid of microcapsules, immersing the thus formed first layer in a second bath of elastomeric material containing the desired amount of microcapsules to form thereon a layer of elastomeric material containing microcapsules with the concentration of said microcapsules increasing progressively from the outer surface to the inner surface thereof, vulcanizing or hardening the thus formed layers, and then stripping the thus formed glove or finger stall from the mold and turning it inside out.

10. A method according to claim 9, including the step of vulcanizing the first layer of elastomeric material prior to immersing in said second bath.

11. A method according to claim 9, including the step of applying a coagulation bath to the mold prior to said step of immersing in said first bath.

12. A method according to claim 9, including the step of applying microcapsules to the first layer by flocking or spraying.

13. A method according to claim 9, wherein said step of immersing in a second bath is conducted for a period of time sufficient to produce film of elastomeric material having a thickness of 180 microns.

14. A method according to claim 9, further comprising the sequential steps of rinsing and drying the thus formed layers after said step of immersing in the second bath.

15. A method of protecting a subject from microbes or other pathogens comprising fitting onto at least one hand of said subject a protective and lubricated glove or finger stall, said glove or finger stall comprising a shaped elastomeric material having an inner surface and an outer surface; rupturable and puncturable microcapsules containing at least one pharmacological agent provided in said elastomeric material and being arranged therein so that the concentration thereof increases progressively from the outer surface to the inner surface, with the concentration at said inner surface being 90 to 95% of the total number of microcapsules present in the elastomeric material; and wherein said 90 to 95% concentration at said inner surface presents an undulated inner contact surface to reduce the points of contact with the user's skin so as to diminish the frictional or adherent forces between the skin and the glove thus making the placing and fitting of the glove or finger stall on the hand easy, the outer surface of said elastomeric material being free of the presence of said microcapsules.

* * * * *